United States Patent [19]

Prisbylla

[11] Patent Number: 5,022,915
[45] Date of Patent: Jun. 11, 1991

[54] SUBSTITUTED 2,4-DIARYLPYRIMIDINES AND THEIR USE AS HERBICIDES

[75] Inventor: Michael P. Prisbylla, Richmond, Calif.

[73] Assignee: ICI Americas Inc., Wilmington, Del.

[21] Appl. No.: 487,334

[22] Filed: Mar. 1, 1990

[51] Int. Cl.$^5$ ............... C07D 239/26; C07D 239/34; C07D 239/52; A01N 43/54
[52] U.S. Cl. .................... 71/92; 544/319; 544/333; 544/335; 544/242; 544/298; 544/122; 544/123
[58] Field of Search ............... 71/92; 544/319, 333, 544/335, 242, 122, 123, 298

[56] References Cited

PUBLICATIONS

Takaya et al., Chemical Abstracts, vol. 105, entry 172492q (1986).
Takatani et al., Chemical Abstracts, vol. 109, entry 170451j (1988).
Machon et al., Chemical Abstracts, vol. 110, entry 192843m (1989).

Primary Examiner—John M. Ford
Attorney, Agent, or Firm—Michael J. Bradley

[57] ABSTRACT

2,4-Diarylpyrimidines of the formula

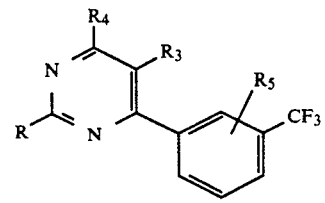

wherein
R is selected from the group consisting of

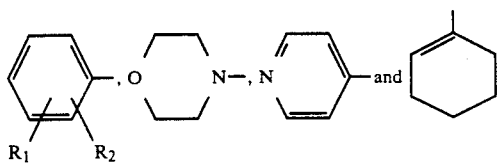

$R_1$ and $R_2$ are independently selected from the group consisting of H, Br, Cl, F, C≡N, $CF_3$ and $OCF_3$;
$R_3$ is selected from the group consisting of H, $C_1$-$C_4$ alkyl, $CO_2CH_3$, $CO_2CH_2CH_3$, $CH_2Cl$, $CH_2OCH_3$, CH=$CH_2$, $C_1$-$C_3$ thioalkyl, and $C_1$-$C_3$ alkoxy;
$R_4$ is selected from the group consisting of H, —OH, $C_1$-$C_4$ alkyl, $C_1$-$C_3$ thioalkyl, $C_1$-$C_3$ alkoxy; and
$R_5$ is selected from the group consisting of H and F are useful as herbicidal agents.

21 Claims, No Drawings

SUBSTITUTED 2,4-DIARYLPYRIMIDINES AND THEIR USE AS HERBICIDES

BACKGROUND AND SUMMARY OF THE INVENTION

This invention relates to substituted 2,4-diarylpyrimidines and to their use in herbicidal formulations. In particular, this invention relates to substituted 2,4-diarylpyrimidines of the formula

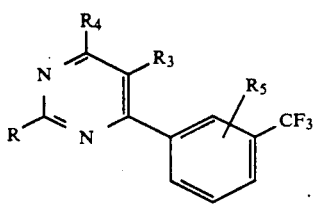

wherein
R is selected from the group consisting of

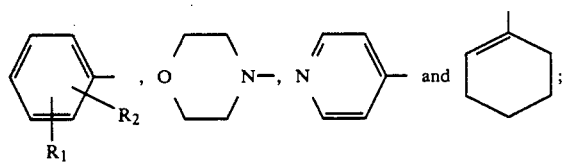

$R_1$ and $R_2$ are independently selected from the group consisting of H, Br, Cl, F, C≡N, $CF_3$ and $OCF_3$;

$R_3$ is selected from the group consisting of H, $C_1$-$C_4$ alkyl, $CO_2CH_3$, $CO_2CH_2CH_3$, $CH_2Cl$, $CH_2OCH_3$, $CH=CH_2$, $C_1$-$C_3$ thioalkyl, and $C_1$-$C_3$ alkoxy;

$R_4$ is selected from the group consisting of H, —OH, $C_1$-$DC_4$ alkyl, $C_1$-$C_3$ thioalkyl, $C_1$-$C_3$ alkoxy; and $R_5$ is selected from the group consisting of H and F.

The compounds of the present invention, as will be seen from the description and test data which follows, have utility as both pre-emergence and post-emergence herbicides, against a wide range of plant species. The preferred method of application is pre-emergence, and is particularly useful on wheat, corn, soy, milo and rice crops in view of its selectivity.

The terms "herbicide" and "herbicidal" are used herein to denote the inhibitive control or modification of undesired plant growth. Inhibitive control and modification include all deviations from natural development such as, for example, total killing, growth retardation, defoliation, desiccation, regulation, stunting, tillering, stimulation, leaf burn, and dwarfing. The term "herbicidally effective amount" is used to denote any amount which achieves such control or modification when applied to the undesired plants themselves or to the area in which these plants are growing. The term "plants" is intended to include germinant seeds, emerging seedlings and established vegetation, including both roots and above-ground portions.

DETAILED DESCRIPTION OF THE INVENTION AND PREFERRED EMBODIMENTS

Within the scope of the above formula, certain embodiments are preferred as follows.
Preferred $R_1$ and $R_2$ groups are F, Cl and $CH_3$.

Preferred $R_3$ groups are $CH_3$ and $C_2CH_5$, and $CH_2OCH_3$ and $CO_2CH_2CH_3$ when $R_4$ is H.

When $R_3$ is H, the preferred $R_4$ group is $CH_2CH_3$.

In the terms "alkyl" "thioalkyl" and "alkoxy", the alkyl group as used herein denotes straight-chain groups. Examples of alkyl groups are methyl, ethyl and n-propyl. Examples of alkoxy groups are methoxy, ethoxy, and n-propoxy.

The compounds of this invention are prepared by a step-wise sequence of reactions as follows:

(a) Diarylpyrimidines which are mono-substituted in the five position 2 are prepared by the condensation enaminoes such as 1 with amidines as shown (J. Heterocyclic Chem, 183 [1981]). The reaction is usually conducted in ethanol, but other solvents such as THF are also suitable. Reaction temperatures vary from room temperature to the boiling point of the selected solvent. Reaction times are determined by monitoring product by Silica gel chromatography and may take several hours.

The required enaminoes are prepared by the action of formamide acteals, such as N,N-dimethylformamide dimethyl acetal and tert butoxy bis(dimethylamino)methane, on alkylphenones. The reaction is carried out in toluene or THF, at room temperature to reflux temperatures.

Alkylphenones necessary here are synthesized by the action of alkyl Grignards on the O,N-dimethylbenzamides 3, as described by S. Nahm and S. M. Weinreb, *tetrahedron Letters*, 3815(1981).

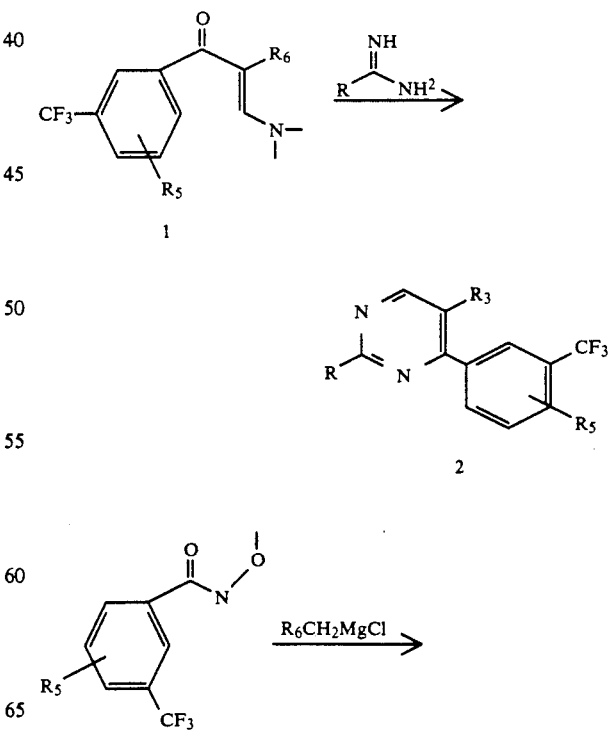

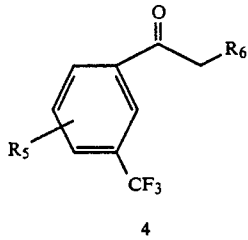

where $R_6$ is $C_1$–$C_4$ akyl, carbethoxy, $C_1$–$C_3$ sulfonyl, etc.

(B) 6-mono-substituted diarylpyrimidines 6 are synthesized by the condensation of acetylenic ketones 5, with amidines. These reactions occur in solvents such as ethanol and THF over the period of a few hours. The acetylenic ketones were again prepared by the method of Weinreb, using lithiated acetylenes 7 and the amides.

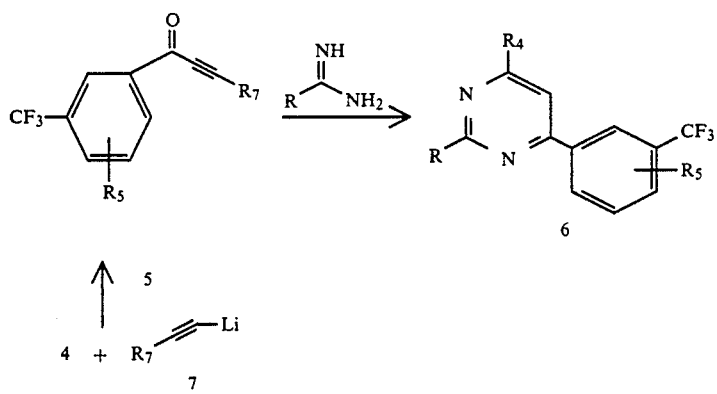

where $R_7$ is $C_1$–$C_4$ alkyl.

(c) Heteroatom substituted pyrimidines in the six position were prepared by the condensation of the B-keto esters and the amidines in refluxing ethanol to generate the hydroxy pyrimidine 9. This hydroxy pyrimidine may have alkyl substitution in the five position, depending on substitution in the B-keto ester. Chlorination of 9 with POCl3 affords the chloropyrimidine 10 which is displaced with various nucleophiles such as alkoxides, amines and thiols forming 11.

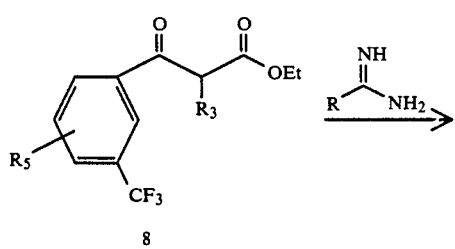

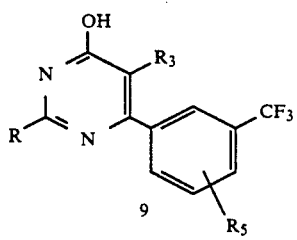

where $R_4$ is OH, $C_1$–$C_3$ thioalkyl or $C_1$–$C_4$ alkoxy.

The following are examples of compounds which have been synthesized by the procedures described above. These examples are offered strictly for purposes of illustration, and are intended neither to limit nor to define the invention in any manner. The compounds were identified by infrared analysis (IR), mass spectroscopy analysis (MS), and nuclear magnetic resonance analysis (NMR).

EXAMPLE 1

Preparation of 2-phenyl-4-(3-trifluoromethylphenyl)-5-ethylpyrimidine

The 1-(trifluoromethylphenyl)-2-(N,N-dimethylaminomethylene)-1-butanone (2.6 grams, 9.6 mmol), benzamidine hydrochloride (1.8 grams, 12.0 mmol) and Na2CO3 (1.27 grams, 12.0 mmol) were heated to reflux in ethanol (50 ml) for six hours. The solution was then cooled and concentrated. The residue was taken up into EtOAc and washed with water, brine (sat.), dried (MgSO4), filtered and concentrated. The residue was chromatographed on Silica gel (hexane/EtOAc, gradient elution) to afford 1.25 grams (40%) of material.

EXAMPLE 2

Preparation of 2-(4'-pyridyl)-4-(3-trifluoromethylphenyl)-6-ethylpyrimidine.

The 1-(3-trifluoromethylphenyl)-2-pentyn-1-one (1.58 grams, 7.0 mmol), 4-amidinopyridine hydrochloride (1.1 grams, 7.0 mmol) and Na2CO3 (0.74 grams, 7.0 mmol) were heated to reflux in ethanol (50 ml) containing water (0.72 grams) for two hours. The mixture was concentrated and the residue taken up into EtOAc and washed with water, brine (sat.), dried (MgSO4), filtered and concentrated. The residue was chromatographed on Silica gel (hexane/EtAOc, gradient elution) to afford 1.3 grams (56%) of product.

EXAMPLE 3

Preparation of 2-(4-fluoropheynl)-4-(3-trifluoromethylphenyl)-5-ethyl-6-triomethylpyrimidine.

To 2-(4-fluorophenyl)-4-(3-trifluoromethylphenyl)-5-ethyl-6-hydroxypyrimidine (2.5 grams, 6.9 mmol) in tolune (7 ml) containing tripropylamine (1.15 grams, 7.9 mmol) was added phosphorus oxychloride (11 grams, 72 mmol). After an exotherm, the solution was refluxed for two hours. The solution was then concentrated, the residue taken up into toluene and washed with NaHCO3, water, brine (sat.), dried (MgSO4), filtered and concentrated to give 2.0 grams of a solid. The chloropyrimidine was then taken up into DMF (20 mL) and was added dropwise to a solution of sodium methyl mercaptan (0.55 grams, 7.88 mmol) in DMF (20 ml) at room temperature and the solution allowed to stir overnight. An additional amount of the mercaptan (0.14 grams, 2.0 mmol) was added and the solution stirred for five hours. An additional amount of the mercaptan (0.10 grams, 1.4 mmol) was again added and the solution stirred for one hour, at which time the solution was poured into water and extracted with EtOAc. The combined extracts were washed with brine (sat.), dried (MgSO4), filtered and concentrated. Purification by Silica gel chromatography (hexane/EtOAc, gradient elution) afforded 0.68 grams (33%) of product.

These and further compounds prepared by similar procedures are listed in Table I below, together with physical data in the form of refractive indices or melting points where such measurements were possible, and physical descriptions where they were not.

TABLE I

| Compound No. | R | R1 | R2 | R3 | R4 | R5 | Physical Constant $n_D^{30}$ or m.p. °C. |
|---|---|---|---|---|---|---|---|
| 1 | 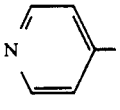 | — | — | CO2CH2CH3 | H | H | 92-95 |
| 2 | 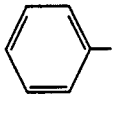 | — | — | CO2CH3 | H | H | 55-86 |
| 3 | 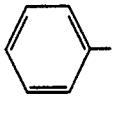 | 4-F | H | CO2CH2CH3 | H | H | 94-96 |
| 4 | 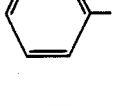 | 2-F | H | CO2CH2CH3 | H | H | 88-91 |
| 5 | 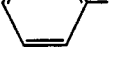 | 3-F | H | CO2CH2CH3 | H | H | 96-99 |
| 6 | 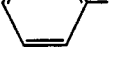 | 3-Cl | H | CO2CH2CH3 | H | H | 105-106 |

TABLE I-continued
| Compound No. | R | R₁ | R₂ | R₃ | R₄ | R₅ | Physical Constant $n_D^{30}$ or m.p. °C. |
|---|---|---|---|---|---|---|---|
| 7 |  | 3-CH₃ | H | CO₂CH₂CH₃ | H | H | 84–90 |
| 8 |  | H | H | CO₂CH₃ | H | H | 123–127 |
| 9 |  | 4-CF₃ | H | CO₂CH₂CH₃ | H | H | 74–76 |
| 10 |  | — | — | CO₂CH₂CH₃ | H | H | 65–72 |
| 11 |  | — | — | CO₂CH₂CH₃ | H | H | 103–105 |
| 12 | 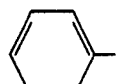 | 4-Cl | H | CO₂CH₂CH₃ | H | H | 90–92 |
| 13 | 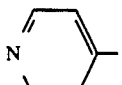 | 4-CN | H | CO₂CH₂CH₃ | H | H | 127–128 |
| 14 | 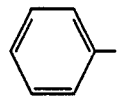 | — | — | CO₂CH₂CH₃ | H | H | 85–88 |
| 15 | 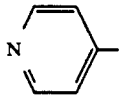 | H | H | CH₃ | H | H | 72–73 |
| 16 | 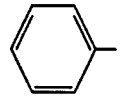 | — | — | CH₃ | H | H | 129–132 |
| 17 | 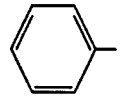 | H | H | CH₂CH₃ | H | H | 74–76 |

TABLE I-continued

Structure: pyrimidine with R at 2-position, R₄ at 4-position (wait) — central scaffold: 2-R, 4-(trifluoromethylphenyl with R₅), 5-R₃, 6-R₄ pyrimidine (as depicted).

| Compound No. | R | R₁ | R₂ | R₃ | R₄ | R₅ | Physical Constant $n_D^{30}$ or m.p. °C. |
|---|---|---|---|---|---|---|---|
| 18 | 4-pyridyl | — | — | $CH_2CH_3$ | H | H | 83–86 |
| 19 | phenyl | 4-Cl | H | $CH_2CH_3$ | H | H | 80–83 |
| 20 | phenyl | 4-F | H | $CH_2CH_3$ | H | H | 50–52 |
| 21 | phenyl | 4-F | H | $CH_3$ | H | H | 70–72 |
| 22 | phenyl | 4-Cl | H | $CH_3$ | H | H | 84–86 |
| 23 | phenyl | H | H | $CH_2CH_2CH_3$ | H | H | 118–121 |
| 24 | phenyl | 4-F | H | $CH_2CH_2CH_3$ | H | H | 84–87 |
| 25 | phenyl | H | H | $CH_2CH_2CH_2CH_3$ | H | H | 65–71 |
| 26 | phenyl | 4-F | H | $CH_2CH_2CH_2CH_3$ | H | H | 81–83 |
| 27 | 4-pyridyl | — | H | $CH_2CH_2CH_2CH_3$ | H | H | 50–53 |
| 28 | 4-pyridyl | — | — | $CH_2CH_2CH_3$ | H | H | 87–89 |

TABLE I-continued
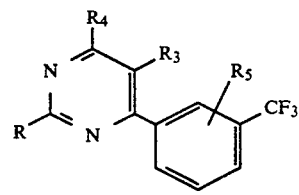
| Compound No. | R | $R_1$ | $R_2$ | $R_3$ | $R_4$ | $R_5$ | Physical Constant $n_D^{30}$ or m.p. °C. |
|---|---|---|---|---|---|---|---|
| 29 | phenyl | 2-F | H | CH₂CH₂CH₃ | H | H | Oil |
| 30 | phenyl | 4-Br | H | CH₂CH₃ | H | H | 81–83 |
| 31 | phenyl | 4-Cl | H | H | CH₂CH₃ | H | 100–101 |
| 32 | phenyl | 4-F | H | H | CH₂CH₂CH₃ | H | 84–86 |
| 33 | phenyl | 4-Cl | H | H | CH₂CH₂CH₃ | H | 71–73 |
| 34 | phenyl | 4-Cl | H | H | CH₃ | H | 90–105 |
| 35 | phenyl | H | H | H | CH₂CH₂CH₃ | H | 66–68 |
| 36 | phenyl | H | H | H | CH₂CH₃ | H | 60–61 |
| 37 | 4-pyridyl | — | — | H | CH₂CH₃ | H | 103–108 |
| 38 | 4-pyridyl | — | — | H | CH₂CH₂CH₃ | H | 86–88 |
| 39 | phenyl | 4-F | H | H | CH₂CH₃ | H | 72–73 |

TABLE I-continued
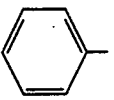
| Compound No. | R | $R_1$ | $R_2$ | $R_3$ | $R_4$ | $R_5$ | Physical Constant $n_D^{30}$ or m.p. °C. |
|---|---|---|---|---|---|---|---|
| 40 | 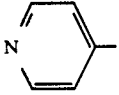 | 4-CH$_3$ | H | H | CH$_2$CH$_3$ | H | 73–74 |
| 41 | 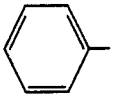 | — | — | H | CH$_3$ | H | 122–124 |
| 42 | 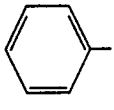 | H | H | H | CH$_3$ | H | 64–66 |
| 43 | 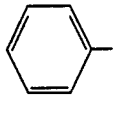 | 4-F | H | H | CH$_3$ | H | 117–118 |
| 44 | 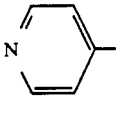 | H | H | H | SCH$_3$ | H | 99–100 |
| 45 | 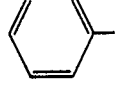 | — | — | H | SCH$_3$ | H | 146–152 |
| 46 | 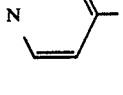 | H | H | H | SCH$_2$CH$_3$ | H | 175–176 |
| 47 | 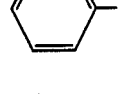 | — | — | H | SCH$_2$CH$_3$ | H | 148–150 |
| 48 |  | 4-Cl | H | H | H | H | 92–94 |
| 49 | 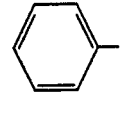 | — | — | H | H | H | 116–118 |
| 50 |  | H | H | H | H | H | 66–68 |

TABLE I-continued
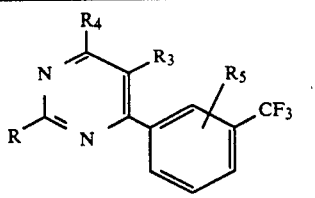
| Compound No. | R | $R_1$ | $R_2$ | $R_3$ | $R_4$ | $R_5$ | Physical Constant $n_D^{30}$ or m.p. °C. |
|---|---|---|---|---|---|---|---|
| 51 | phenyl | 4-Cl | H | H | $CH_2CH_3$ | H | 124–125 |
| 52 | phenyl | — | — | $CH_2CH_3$ | $SCH_3$ | H | 100–106 |
| 53 | phenyl | —F | H | $CH_2Cl$ | H | H | 105–106 |
| 54 | phenyl | 4-F | H | $CH_2CH=CH_2$ | H | H | 87–89 |
| 55 | phenyl | 4-F | H | $CH_2OCH_3$ | H | H | 85–87 |
| 56 | phenyl | 4-Cl | H | $OCH_3$ | H | H | 122–123 |
| 57 | phenyl | 4-F | H | $OCH_3$ | H | H | 95–96 |
| 58 | 4-pyridyl | — | H | $OCH_3$ | H | H | 131–132.5 |
| 59 | phenyl | 3-F | H | $OCH_3$ | H | H | 67–69 |
| 60 | phenyl | H | H | $OCH_3$ | H | H | 93–95 |
| 61 | phenyl | 4-$OCH_3$ | H | $OCH_3$ | H | H | 105–106 |

TABLE I-continued

[Structure diagram showing pyrimidine with substituents R, R3, R4, R5, CF3]

| Compound No. | R | R1 | R2 | R3 | R4 | R5 | Physical Constant $n_D^{30}$ or m.p. °C. |
|---|---|---|---|---|---|---|---|
| 62 | [phenyl] | — | — | CH2CH3 | | H | 2-F |

The compounds listed in the foregoing table were tested for herbicidal activity by various methods and at various rates of application. The results of some of these tests are given below. As one skilled in the art is aware, the results obtained in herbicidal screening tests are affected by a number of factors that are not readily controllable. Environmental conditions such as amount of sunlight and water, soil type, soil pH, temperature and humidity, are examples of such factors. The depth of planting and the application rate of the herbicide, as well as the nature of crops being tested, can also effect the test results. Results will also vary from crop to crop and within the crop varieties.

The test procedures used are as follows:

Pre-Emergence Herbicidal Evaluation at 4 lb/acre

Planting flats were filled with sandy loam soil containing a fungicide and fertilizer. The soil was leveled and rows of grassy weeds and broadleaf weeds were planted thickly enough so that several seedlings emerged per inch of row. The grassy weeds were green foxtail (*Setaria viridis*), watergrass (*Echinochloa crusgalli*) and wild oats (*Avena fatua*). Broadleaf weeds utilized were annual morninqglory (*Ipomoea purpurea*), velvetleaf (*Abutilon theophrasti*), wild mustard (*Brassica kaber*), and yellow nutsedge (*Cyperus esculentus*).

Solutions of the test compounds were made by weighing out 333 mg of the test compound into a 60-mL wide-mouth bottle, then dissolving the compound in 25 mL of acetone containing 1% Tween ® 20 (polyoxyethylene sorbitan monolaurate emulsifier). Additional solvents, not exceeding 5 mL, were used if needed to dissolve the compound. A 20.5-mL aliquot was then taken from the solution and diluted with 25 mL of an acetone:water mixture (19:1) containing 1% Tween ® 20. This was used as the spray solution.

One day after planting, the flats were sprayed with the spray solution at a rate of 80 gallons of solution per acre with the compound being applied at a rate of 4 pounds per acre (4.48 kg/hectare).

The flats were then returned to the greenhouse and watered daily by sprinkling. The degree of weed control was estimated and recorded 3 weeks after treatment, as percentage control compared to the growth of the same species in an untreated check flat of the same age.

The percent control is the total injury to the plants due to all factors, including inhibited germination, killing of the plant tissue after emergence, stunting, malformation, chlorosis, and other types of injury. The control ratings vary from 0 to 100 percent, where 0 represents no effect with growth equal to the untreated control, and 100 represents complete kill; a dash indicates that no test was performed at that level of application.

Post-Emergence Herbicidal Evaluation at 4 lb/acre

The soil was prepared and seeded with the same varieties used in the pre-emergence test. The flats were placed in the greenhouse at 70-85° F. (21-29° C.) and watered by sprinkling. Twelve to fourteen days after planting, the flats were sprayed at a rate of 80 gallons of solution per acre. Each compound was applied at the rate of 4 pounds/acre (4.48 kg/hectare), using a spray solution prepared as in the pre-emergence test.

The flats were returned to the greenhouse after spraying and watered daily without wetting the foliage. Three weeks after treatment, the degree of weed control was estimated and recorded as percentage control compared to the growth of the same species in an untreated check flat of the same age. The percent control ratings were assigned on the same basis as for the pre-emergence evaluation.

The following table lists the results of these tests, in terms of averages for the grasses and broadleaf weeds listed separately, in both pre- and post-emergence evaluations.

TABLE II

Herbicidal Test Results - Percent Control at 4 lb/A

| Compound No. | Pre-Emergence | | Post-Emergence | |
|---|---|---|---|---|
| | AVG | AVB | AVG | AVB |
| 1 | 50 | 37 | 0 | 0 |
| 2 | 68 | 87 | 47 | 73 |
| 3 | 83 | 80 | 13 | 67 |
| 4 | 47 | 38 | 0 | 43 |
| 5 | 47 | 53 | 27 | 47 |
| 6 | 33 | 23 | 0 | 0 |
| 7 | 67 | 47 | 0 | 47 |
| 8 | 47 | 40 | 0 | 0 |
| 9 | 50 | 40 | 0 | 40 |
| 10 | 73 | 40 | 0 | 50 |
| 11 | 83 | 87 | 20 | 73 |
| 12 | 60 | 73 | 0 | 100 |
| 13 | 33 | 0 | 0 | 37 |
| 14 | 77 | 85 | 67 | 80 |
| 15 | 93 | 67 | 47 | 73 |
| 16 | 93 | 73 | 70 | 80 |
| 17 | 93 | 98 | 93 | 97 |
| 18 | 100 | 100 | 93 | 80 |
| 19 | 87 | 87 | 27 | 67 |
| 20 | 100 | 100 | 90 | 90 |
| 21 | 100 | 100 | 87 | 80 |
| 22 | 95 | 77 | 67 | 73 |
| 23 | 70 | 73 | 43 | 73 |
| 24 | 100 | 85 | 73 | 80 |
| 25 | 78 | 73 | 13 | 70 |
| 26 | 73 | 57 | 20 | 80 |

TABLE II-continued

Herbicidal Test Results - Percent Control at 4 lb/A

| Compound No. | Pre-Emergence AVG | Pre-Emergence AVB | Post-Emergence AVG | Post-Emergence AVB |
|---|---|---|---|---|
| 27 | 95 | 100 | 93 | 82 |
| 28 | 97 | 100 | 97 | 95 |
| 29 | 95 | 87 | 0 | 0 |
| 30 | 85 | 57 | 63 | 80 |
| 31 | 93 | 87 | 47 | 70 |
| 32 | 90 | 80 | 60 | 73 |
| 33 | 87 | 80 | 57 | 57 |
| 34 | 70 | 40 | 0 | 17 |
| 35 | 70 | 47 | 27 | 67 |
| 36 | 100 | 97 | 83 | 85 |
| 37 | 95 | 97 | 70 | 82 |
| 38 | 77 | 78 | 65 | 60 |
| 39 | 98 | 98 | 73 | 80 |
| 40 | 87 | 57 | 7 | 53 |
| 41 | 77 | 53 | 55 | 60 |
| 42 | 93 | 68 | 78 | 63 |
| 43 | 83 | 80 | 72 | 63 |
| 44 | 47 | 53 | 7 | 57 |
| 45 | 77 | 97 | 7 | 60 |
| 46 | 40 | 50 | 48 | 97 |
| 47 | 10 | 33 | 3 | 27 |
| 48 | 43 | 40 | 0 | 27 |
| 49 | 37 | 3 | 0 | 0 |
| 50 | 10 | 0 | 0 | 0 |
| 56 | 90 | 60 | 50 | 90 |
| 57 | 100 | 100 | 85 | 90 |
| 58 | 80 | 90 | 90 | 90 |

Abbreviations:
AVG Grasses averaged
AVB Broadleaf weeds averaged

The compounds of the present invention are useful as herbicides and can be applied in a variety of ways known to those skilled in the art, at various concentrations. In practice, the compounds are applied as formulations containing the various adjuvants and carriers known to or used in the industry for facilitating dispersion. The choice of formulation and mode of application for any given compound may affect its activity, and selection will be made accordingly. The compounds of the invention may thus be formulated as granules, as wettable powders, as emulsifiable concentrates, as powders or dusts, as flowables, as solutions, suspensions or emulsions, or in controlled-release forms such as microcapsules. These formulations may contain as little as about 0.5% to as much as amount 95% or more by weight of active ingredient. The optimum amount for any given compound will depend upon the nature of the seeds or plants to be controlled. The rate of application will generally vary from about 0.01 to about 10 pounds per acre, preferably from about 0.02 to about 4 pounds per acre.

Wettable powders are finely divided particles which disperse readily in water or other liquid carriers. The particles contain the active ingredient retained in a solid matrix. Typical solid matrices include fuller's earth, kaolin clays, silicas and other readily wet organic or inorganic solids. Wettable powders normally contain about 5% to about 95% of the active ingredient plus a small amount of wetting, dispersing, or emulsifying agent.

Emulsifiable concentrates are homogeneous liquid compositions dispersible in water or other liquid, and may consist entirely of the active compound with a liquid or solid emulsifying agent, or may also contain a liquid carrier, such as xylene, heavy aromatic naphthas, isophorone and other non-volatile organic solvents. In use, these concentrates are dispersed in water or other liquid and normally applied as a spray to the area to be treated. The amount of active ingredient may range from about 0.5% to about 95% of the concentrate.

Granular formulations include both extrudates and relatively coarse particles, and are usually applied without dilution to the area in which suppression of vegetation is desired. Typical carriers for granular formulations include sand, fuller's earth, attapulgite clay, bentonite clays, montmorillonite clay, vermiculite, perlite and other organic or inorganic materials which absorb or which can be coated with the active compound. Granular formulations normally contain about 5% to about 25% active ingredients which may include surface-active agents such as heavy aromatic naphthas, kerosene and other petroleum fractions, or vegetable oils; and/or stickers such as dextrins, glue or synthetic resins.

Dusts are free-flowing admixtures of the active ingredient with finely divided solids such as talc, clays, flours and other organic and inorganic solids which act as dispersants and carriers.

Microcapsules are typically droplets or granules of the active material enclosed in an inert porous shell which allows escape of the enclosed material to the surroundings at controlled rates. Encapsulated droplet are typically about 1 to 50 microns in diameter. The enclosed liquid typically constitutes about 50% to 95% of the weight of the capsule, and may include solvent in addition to the active compound. Encapsulated granules are generally porous granules with porous membranes sealing the granule pore openings, retaining the active species in liquid form inside the granule pores. Granules typically range from 1 millimeter to 1 centimeter, preferably 1 to 2 millimeters in diameter. Granules are formed by extrusion, agglomeration or prilling, or are naturally occurring. Examples of such materials are vermiculite, sintered clay, kaolin, attapulgite clay, sawdust and granular carbon. Shell or membrane materials include natural and synthetic rubbers, cellulosic materials, styrene-butadiene copolymers, polyacrylonitriles, polyacrylates, polyesters, polyamides, polyureas, polyurethanes and starch xanthates.

Other useful formulations for herbicidal applications include simple solutions of the active ingredient in a solvent in which it is completely soluble at the desired concentration, such as acetone, alkylated naphthalenes, xylene and other organic solvents. Pressurized sprayers, wherein the active ingredient is dispersed in finely-divided form as a result of vaporization of a low boiling dispersant solvent carrier, such as the Freons, may also be used.

Many of these formulations include wetting, dispersing or emulsifying agents. Examples are alkyl and alkylaryl sulfonates and sulfates and their salts; polyhydric alcohols; polyethoxylated alcohols; esters and fatty amines. These agents when used normally comprise from 0.1% to 15% by weight of the formulation.

The compounds of the present invention are also useful when combined with other herbicides and/or defoliants, dessicants, growth inhibitors, and the like. These other materials can comprise from about 5% to about 95% of the active ingredients in the formulations. These combinations frequently provided a higher level of effectiveness in controlling weeds and often provide results unattainable with separate formulations of the individual herbicides.

Examples of other herbicides, defoliants, dessicants and plant growth inhibitors with which the compounds of this invention can be combined are:

chlorophenoxy herbicides such as 2,4-D, 2,4,5-T, MCPA, MCPB, 2,4-DB, 2,4-DEB, 4-CPA, 2,4,5-TB, and silvex;

carbamate herbicides such as propham, chlorpropham, swep, and barban;

thiocarbamate and dithiocarbamate herbicides such as CDEC, metham-sodium, EPTC, diallate, PEBC, and vernolate;

substituted urea herbicides such as norea, dichloral, urea, chloroxuron, cycluron, fenuron, monuron, monuron TCA, diuron, linuron, monolinuron neburon, buturon and trimeturon;

symmetrical triazine herbicides such as simazine, chlorazine, desmetryne, norazine, ipazine, prometryn, atrazine, trietazine, simetone, prometone, propazine and ametryne;

chlorinated aliphatic acid herbicides such as TCA and dalapon;

chlorinated benzoic acid and phenylacetic acid herbicides such as 2,3,6-TBA, dicamba, tricamba, chloramben, fenac, PBA, 2-methoxy-3,6-dichlorophenyl acetic acid, 3-methoxy-2,6-dichlorophenyl acetic acid, 2-methoxy-3,5,6-trichlorophenyl acetic acid, and 2,4-dichloro-3-nitro benzoic acid;

and such compounds as aminotriazole, maleic hydrazide, phenylmercury acetate, endothal, technical chlordane, DCPA, diquat, erbon, DNC, DNBP, dichlobenil, DPA, diphenamide, dipropalin, trifluralin, solan, dicryl, merphos, DMPA, DSMA, MSMA, potassium azide, acrolein, benefin, bensulide, AMS, bromacil, 2-(3,4-dichlorophenyl)-4-methyl-1,2,4-oxazolidine-3,5-dione, bromoxynil, cacodylic acid, CMA, CPMF, cypromid, DCB, DCPA, dichlone, diphenatril, DMTT, DNAP, EBEP, EXD, HCA, ioxynil, IPX, isocil, potassium cyanate, MAA, MAMA, MCPES, MCPP, MH, molinate, NPA, OCH, paraquat, PCP, picloram, DPA, PCA, sesone, terbacil, terbutol, TCBA, alachlor, nitralin, sodium tetraborate, calcium cyanamide, S,S,S-tributylphosphorotrithioate and propanil.

These formulations can be applied to the areas where control is desired by conventional methods. Dust and liquid compositions, for example, can be applied by the use of power-dusters, boom and hand sprayers and spray dusters. The formulations can also be applied from airplanes as a dust or a spray or by rope wick applications. To modify or control growth of germinating seeds or emerging seedlings, dust and liquid formulations can be distributed in the soil to a depth of at least one-half inch below the soil surface or applied to the soil surface only, by spraying or sprinkling. The formulations can also be applied by addition to irrigation water. This permits penetration of the formulations into the soil together with the irrigation water. Dust compositions, granular compositions or liquid formulations applied to the surface of the soil can be distributed below the surface of the soil by conventional means such as discing, dragging or mixing operations.

The following are examples of typical formulations.

| | |
|---|---|
| 5% dust | 5 parts active compound |
| | 95 parts talc |
| 2% dust | 2 parts active compound |
| | 1 part highly dispersed silicic acid |
| | 97 parts talc |

These dusts are formed by mixing the components then grinding the mixture to the desired particle size.

| | |
|---|---|
| 5% granules | 5 parts active compound |
| | 0.25 part epichlorohydrin |
| | 0.25 part cetyl polyglycol ether |
| | 3.5 parts polyethylene glycol |
| | 91 parts kaolin (particle size 0.3–0.8 mm) |

Granules are formed by mixing the active compound with epichlorohydrin and dissolving the mixture in 6 parts of acetone. The polyethylene glycol and cetyl polyglycol ether are then added. The resultant solution is sprayed on the kaolin and the acetone evaporated in vacuo.

| wettable powders: | |
|---|---|
| 70% | 70 parts active compound |
| | 5 parts sodium dibutylnaphthylsulfonate |
| | 3 parts naphthalenesulfonic acid/phenolsulfonic acid/formaldehyde condensate (3:2:1) |
| | 10 parts kaolin |
| | 12 parts Champagne chalk |
| 40% | 40 parts active compound |
| | 5 parts sodium lignin sulfonate |
| | 1 part sodium dibutylnaphthalene sulfonic acid |
| | 54 parts silicic acid |
| 25% | 25 parts active compound |
| | 4.5 parts calcium lignin sulfate |
| | 1.9 parts Champagne chalk/hydroxyethyl cellulose (1:1) |
| | 1.5 parts sodium dibutylnaphthalene sulfonate |
| | 19.5 silicic acid |
| | 19.5 parts Champagne chalk |
| | 28.1 parts kaolin |
| 25% | 25 parts active compound |
| | 2.5 parts isooctylphenoxy-polyethylene-ethanol |
| | 1.7 parts Champagne chalk/hydroxyethyl cellulose (1:1) |
| | 8.3 parts sodium aluminum silicate |
| | 16.5 parts kieselguhr |
| | 46 parts kaolin |
| 10% | 10 parts active compound |
| | 3 parts of a mixture of sodium salts of saturated fatty alcohol sulfates |
| | 5 parts naphthalenesulfonic acid/formaldehyde condensate |
| | 82 parts kaolin |

These wettable powders are prepared by intimately mixing the active compounds with the additives in suitable mixers, and grinding the resulting mixture in mills or rollers.

| emulsifiable concentrate: | |
|---|---|
| 25% | 25 parts active substance |
| | 2.5 parts epoxidized vegetable oil |
| | 10 parts of an alkylarylsulfonate/fatty alcohol polyglycol ether mixture |
| | 5 parts dimethylformamide |
| | 57.5 parts xylene |

What is claimed is:
1. A compound having the formula

23

[Structure: pyrimidine with R at 2-position, R4 at 4, R3 at 5, and 6-position bearing phenyl with R5 and CF3]

wherein
R is selected from the group consisting of

[Three substituent structures: phenyl with R1, R2; morpholine (O, N—); pyridin-4-yl; and cyclohexenyl with methyl]

R₁ and R₂ are independently selected from the group consisting of H, Br, Cl, F, C≡N, CF₃ and OCF₃;
R₃ is selected from the group consisting of H, C₁-C₄ alkyl, CH₂cl, CH₂OCH₃, CH=CH₂, C₁-C₃ thioalkyl, and C₁-C₃ alkoxy;
R₄ is selected from the group consisting of H, —OH, C₁-C₄ alkyl, C₁-C₃ thioalkyl, C₁-C₃ alkoxy; and
R₅ is selected from the group consisting of H and F.

2. The compound of claim 1 wherein R is

[phenyl]

R₁ is H, R₂ is H, R₃ is CH₂CH₃, R₄ is H and R₅ is H.

3. The compound of claim 1 wherein R is

[phenyl]

R₁ is H, R₂ is 4-F, R₃ is CH₂CH₃, R₄ is H and R₅ is H.

4. The compound of claim 1 wherein R is

[pyridin-4-yl]

R₃ is CH₂CH₃, R₄ is H and R₅ is H.

5. The compound of claim 1 wherein R is

[phenyl]

R₁, is H, R₂ is H, R₃ is H, R₄ is CH₂CH₃ and R₅ is H.

6. The compound of claim 1 wherein R is

[phenyl]

R₁ is H, R₂ is 4-F, R₃ is H, R₄ is CH₂CH₃ and R₅ is H.

7. The compound of claim 1 wherein R is

[pyridin-4-yl]

R₃ is H, R₄ is CH₂CH₃ and R₅ is H.

8. An herbicidal composition comprising:
(a) an herbicidally effective amount of a compound having the formula

[Structure: same pyrimidine as above]

wherein
R is selected from the group consisting of

[Same four substituent structures]

R₁₂ and R₂ are independently selected from the group consisting of H, Br, Cl, F, C≡N, CF₃ and OCF₃;
R₃ is selected from the group consisting of H, C₁-C₄ alkyl, CO₂CH₃, CO₂CH₂CH₃, CH₂l, CH₂OCH₃, CH=CH₂, C₁-C₃ thioalkyl, and C₁-C₃ alkoxy;
R₄ is selected from the group consisting of H, —OH, C₁-C₄ alkyl, C₁-C₃ thioalkyl, C₁-C₃ alkoxy; and
R₅ is selected from the group consisting of H and F;
(b) an herbicidally acceptable diluent or carrier.

9. The composition of claim 8 wherein R is

[phenyl]

R₁ is H, R₂ is H, R₃ is CH₂CH₃, R₄ is H and R₅ is H.

10. The composition of claim 8 wherein R is

[phenyl]

R₁ is H, R₂ is 4-R, R₃ is CH₂CH₃, R₄ is H and R₅ is H.

11. The composition of claim 8 wherein R is

[pyridin-4-yl]

$R_3$ is $CH_2CH_3$, $R_4$ is H and $R_5$ is H.

12. The composition of claim 8 wherein R is

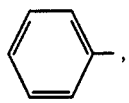

$R_1$ is H, $R_2$ is H, $R_3$ is H, $R_4$ is $CH_2CH_3$ and $R_5$ is H.

13. The composition of claim 8 wherein R is

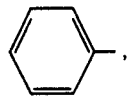

$R_1$ is H, $R_2$ is 4-F, $R_3$ is H, $R_4$ is $CH_2CH_3$ and $R_5$ is H.

14. The composition of claim 8 wherein R is

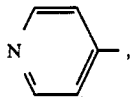

$R_3$ is H, $R_4$ is $CH_2CH_3$ and $R_5$ is H.

15. A method of controlling undesirable vegetation comprising applying to said vegetation or to the locus thereof an herbicidally effective amount of a compound having the formula

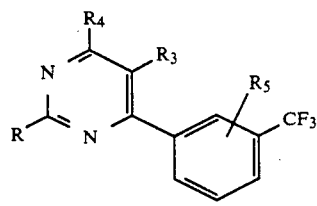

wherein

R is selected from the group consisting of

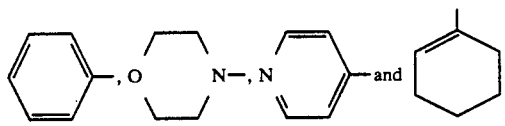

$R_1$ and $R_2$ are independently selected from the group consisting of H, Br, Cl, F, C≡N, $CF_3$ and $OCF_3$;

$R_3$ is selected from the group consisting of H, $C_1$–$C_4$ alkyl, $CO_2CH_3$, $CO_2CH_2CH_3$, $CH_2Cl$, $CH_2OCH_3$, $CH=CH_2$ $C_1$–$C_3$ thioalkyl, and $C_1$–$C_3$ alkoxy;

$R_4$ is selected from the group consisting of H, —OH, $C_1$–$C_4$ alkyl, $C_1$–$C_3$ thioalkyl, $C_1$–$C_3$ alkoxy; and $R_5$ is selected from the group consisting of H and F.

16. The composition of claim 8 wherein R is

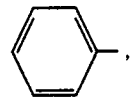

$R_1$ is H, $R_2$ is H, $R_3$ is $CH_2CH_3$, $R_4$ is H and $R_5$ is H.

17. The composition of claim 8 wherein R is

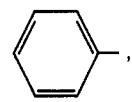

$R_1$ is H, $R_2$ is F-4, $R_3$ is $CH_2CH_3$, $R_4$ is H and $R_5$ is H.

18. The composition of claim 8 wherein R is

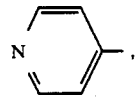

$R_3$ is $CH_2CH_3$, $R_4$ is H and $R_5$ is H.

19. The composition of claim 8 wherein R is

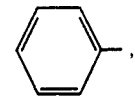

$R_1$ is H, $R_2$ is H, $R_3$ is H, $R_4$ is $CH_2CH_3$ and $R_5$ is H.

20. The composition of claim 8 wherein R is

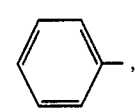

$R_1$ is H, $R_2$ is 4-F, $R_3$ is H, $R_4$ is $CH_2CH_3$ and $R_5$ is H.

21. The composition of claim 8 wherein R is

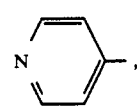

$R_3$ is H, $R_4$ is $CH_2CH_3$ is $R_5$ is H.

* * * * *